US011548918B2

(12) United States Patent
Chen

(10) Patent No.: US 11,548,918 B2
(45) Date of Patent: Jan. 10, 2023

(54) SODIUM CHANNEL PROTEIN NAV1.4-TARGETING POLYPEPTIDE AND USE THEREOF

(71) Applicant: Mengru Chen, Guangzhou (CN)

(72) Inventor: Mengru Chen, Guangzhou (CN)

(73) Assignee: Mengru Chen, Guangzhou (CN)

( * ) Notice: Subject to any disclaimer, the term of this patent is extended or adjusted under 35 U.S.C. 154(b) by 0 days.

(21) Appl. No.: 17/329,194

(22) Filed: May 25, 2021

(65) Prior Publication Data

US 2022/0242915 A1 Aug. 4, 2022

(30) Foreign Application Priority Data

Jan. 29, 2021 (CN) ........................ 202110129660.X

(51) Int. Cl.

*C07K 14/00* (2006.01)
*A61P 17/00* (2006.01)
*A61K 38/00* (2006.01)

(52) U.S. Cl.

CPC ............ *C07K 14/001* (2013.01); *A61P 17/00* (2018.01); *A61K 38/00* (2013.01)

(58) Field of Classification Search

None

See application file for complete search history.

(56) References Cited

PUBLICATIONS

Dworakowska and Dolowy "Ion channels-related diseases" Acta Biochimica Polonica 47:685-703. (Year: 2000).*
Anonymous "Cystic Fibrosis" CDC. https://www.cdc.gov/genomics/disease/cystic_fibrosis.htm (Year: 2020).*
Nicole and Lory "New Challenges Resulting From the Loss of Function of NaV1.4 in Neuromuscular Diseases" Frontiers in Pharmacology 12:751095 (Year: 2021).*

* cited by examiner

*Primary Examiner* — Sudhakar Katakam
*Assistant Examiner* — Zachary J Miknis
(74) *Attorney, Agent, or Firm* — Bayramoglu Law Offices LLC

(57) ABSTRACT

A sodium channel protein Nav1.4-targeting polypeptide is disclosed, which has an amino acid sequence of SEQ ID NO:1. The polypeptide includes a first disulfide bond between Cys-3 and Cys-17, a second disulfide bond between Cys-4 and Cys-23, and a third disulfide bond between Cys-12 and Cys-24. The polypeptide has a complex coiled structure consisting of a main chain and disulfide bonds, in which three key residues $LYS^{10}$, $ARG^{18}$, and $ARG^{22}$ could interact with Nav1.4 and be essential to block its penetrability of sodium. The polypeptide can target sodium channel protein Nav1.4 to form a stable protein complex; compared with naturally extracted drugs, the polypeptide Nav1.4 is superior in terms of yield, production, and cost saving, making it a promising Nav-targeting drug with broad application prospects.

5 Claims, 5 Drawing Sheets

Specification includes a Sequence Listing.

SEQUENCE LISTING

```
<160> NUMBER OF SEQ ID NOS: 1

<210> SEQ ID NO 1
<211> LENGTH: 24
<212> TYPE: PRT
<213> ORGANISM: Artificial Sequence
<220> FEATURE:
<223> OTHER INFORMATION: The sequence is synthesized.

<400> SEQUENCE: 1

Gly His Cys Cys Gly Asp Glu Tyr Arg Lys Trp Cys Gly Lys Arg Val
1               5                   10                  15

Cys Arg Asn Lys Ala Arg Cys Cys
            20
```

SODIUM CHANNEL PROTEIN NAV1.4-TARGETING POLYPEPTIDE AND USE THEREOF

CROSS REFERENCE TO THE RELATED APPLICATIONS

This application is based upon and claims priority to Chinese Patent Application No. 202110129660.X, filed on Jan. 29, 2021, the entire contents of which are incorporated herein by reference.

TECHNICAL FIELD

The present invention relates to the technical field of biomedicine, and particularly relates to a sodium channel protein Nav1.4-targeting polypeptide and use thereof.

BACKGROUND

Voltage-gated sodium channels (Nav) are one type of important transmembrane proteins widely present in human body, regulating a variety of physiological processes such as the secretion of neurotransmitters, vasoconstriction, and skeletal muscle excitability, by generation of action potentials. So far, mutations of Nav channels have been found to be associated with several human diseases, such as epilepsy, arrhythmia, muscle paralysis, paramyotonia, pain syndrome, and autism. Among others, the voltage-gated sodium channel 1.4 (Nav1.4) is encoded by SCN4A and predominantly expressed in skeletal muscle. Nav1.4 can regulate generation of endplate potentials at neuromuscular junctions and the spread of depolarizations along the membranes of the T-tubules, and thereby initiate and regulate skeletal muscle contraction. So far, mutations in Nav1.4 have been found to be associated with at least five hereditary diseases including hyperkalemic periodic paralysis, hypokalemic periodic paralysis, paramyotonia, potassium-aggravated amyosthenia, and congenital myasthenic syndrome, and therefore it has been attracting focus as the target of therapeutic drugs.

Polypeptides have been promising approach of drug development for their highly specific targeting capacity and safety. Currently, predicting the binding mode and affinity between a polypeptide and a target protein through molecular simulation and docking has become an important technology in the field of computer-aided drug research.

There is an urgent need to study and develop compounds that can specifically target the sodium channel protein Nav1.4, which provides a basis for the development of new drugs for the treatment of human-related diseases in the future.

SUMMARY

A first object of the present invention is, in order to address the prior art deficiencies, to provide a novel polypeptide (named NaV-B) that targets the sodium channel protein Nav1.4. The polypeptide has a complex coiled structure consisting of a main chain and a disulfide bond, and can stably target the sodium channel protein Nav1.4.

A second object of the present invention is, in order to address the prior art deficiencies, to provide the use of the novel Nav1.4-targeting polypeptide NaV-B in preparing pharmaceutical compositions for treating channelopathies (ion channels-related diseases).

The objects will be realized by providing a novel polypeptide (NaV-B) that targets the sodium channel protein Nav1.4, wherein the polypeptide (NaV-B) has an amino acid sequence of SEQ ID NO: 1.

The polypeptide has a complex coiled structure consisting of a main chain and disulfide bonds, in which three key residues $LYS^{10}$, $ARG^{18}$, and $ARG^{22}$ could interact with Nav1.4 and be essential to block its penetrability of sodium.

The disulfide bonds include a first disulfide bond between Cys-3 and Cys-17 (i.e., between the cysteine residue at the third position and the cysteine residue at the seventeenth position), a second disulfide bond between Cys-4 and Cys-23 (i.e., between the cysteine residue at the fourth position and the cysteine residue at the twenty-third position), and a third disulfide bond between Cys-12 and Cys-24 (i.e., between the cysteine residue at the twelfth position and the cysteine residue at the twenty-fourth position).

By its three amino acid sites $LYS^{10}$, $ARG^{18}$, and $ARG^{22}$, the polypeptide NaV-B is capable of targeting four domains of Nav1.4: $ASP^{406}$-$GLU^{409}$, $LYS^{1244}$-$GLU^{1248}$, $GLU^{761}$-$GLU^{764}$, and $ASP^{1539}$-$ASN^{1548}$.

The present invention also provides the use of the novel polypeptide NaV-B in preparing pharmaceutical compositions for treating ion channels-related diseases (or channelopathies). Specifically, the invention provides a method for treating ion channels-related diseases, comprising administering to a subject in need thereof an effective amount of the polypeptide NaV-B or a composition comprising the polypeptide NaV-B as an active ingredient.

The present invention also provides a pharmaceutical composition for treating ion channels-related diseases, which comprises the polypeptide NaV-B as an active ingredient. The composition may also comprise a pharmaceutically acceptable carrier.

Specifically, the diseases as mentioned above are sodium channel-related diseases.

Specifically, the diseases (or channelopathies) comprise hyperkalemic periodic paralysis, hypokalemic periodic paralysis, paramyotonia, potassium-aggravated amyosthenia, and congenital myasthenic syndrome, and facial and body wrinkles caused by muscle tension.

The present invention also provides the dynamic simulation analysis of the complex of polypeptide NaV-B and ion channel protein Nav1.4. The RMSD values illustrated that the activities of the complex and Nav1.4 crystal both tend to become stable, indicating that the complex had changed little in stability as compared with the crystal structure of Nav1.4.

Beneficial Effects of the Present Invention:

A novel polypeptide named NaV-B has been developed. The polypeptide has an amino acid sequence of GHCCGDEYRKWCGKRVCRNKARCC, and retains the key blocking residues $LYS^{10}$, $ARG^{18}$, and $ARG^{12}$. Prediction of three-dimensional structure showed that, the polypeptide NaV-B has a complex coiled structure consisting of a main chain and disulfide bonds, and can target sodium channel protein Nav1.4 to form a stable protein complex, which thereby effectively inhibits the changes in membrane potential caused by sodium channel protein Nav1.4 (accordingly, the present invention also provides a method of inhibiting the changes in membrane potential caused by sodium channel protein Nav1.4, comprising administering to a subject in need thereof an effective amount of the polypeptide NaV-B or a composition comprising the polypeptide NaV-B as an active ingredient). The polypeptide NaV-B of the present invention can stably target the sodium channel protein Nav1.4, and is produced by artificial synthesis; compared with naturally extracted drugs, the polypeptide Nav1.4 is superior in terms of yield, production, and cost saving, making it a promising Nav-targeting drug with broad application prospects.

BRIEF DESCRIPTION OF THE DRAWINGS

The drawings are provided to further illustrate the present invention rather than limit the present invention.

DETAILED DESCRIPTION OF THE EMBODIMENTS

The present invention will be further described with the following embodiments and the drawings.

1. Design of Polypeptide NaV-B

By comparing the amino acid sequences of various Nav1.4-blocking molecules using Vector NTI 10.3, homologous series were obtained. The results were edited using BioEdit and thereby the sequence of the polypeptide NaV-B was obtained: GHCCGDEYRKWCGKRVCRNKARCC.

2. Prediction of Three-Dimensional Structure of Polypeptide NaV-B

Prediction of the three-dimensional structure of the polypeptide NaV-B was performed by MODELLER:

(1) NaV-B.ali and pdb_95.pir files were prepared.

(2) We ran command "prf.build ( )" to search for pdb templates of structures similar to the target gene. The output results were stored in the NaV-Bout.prf file, wherein the first six lines recorded the relevant parameters of MODELLER to build this file, and the subsequent lines recorded the similar structures detected by "prf.build ( )". Templates with higher similarities and lower E value were selected.

(3) We downloaded the pdb document of the above candidate templates from the pdb template database, and ran command "for ( ) in ( )" to determine the best template.

(4) Command "automodel ( )" was run in the MODELLER window to obtain the protein prediction results.

(5) The result with the lowest DOPE score and the highest GA341 was selected as the best model.

Figure 1:
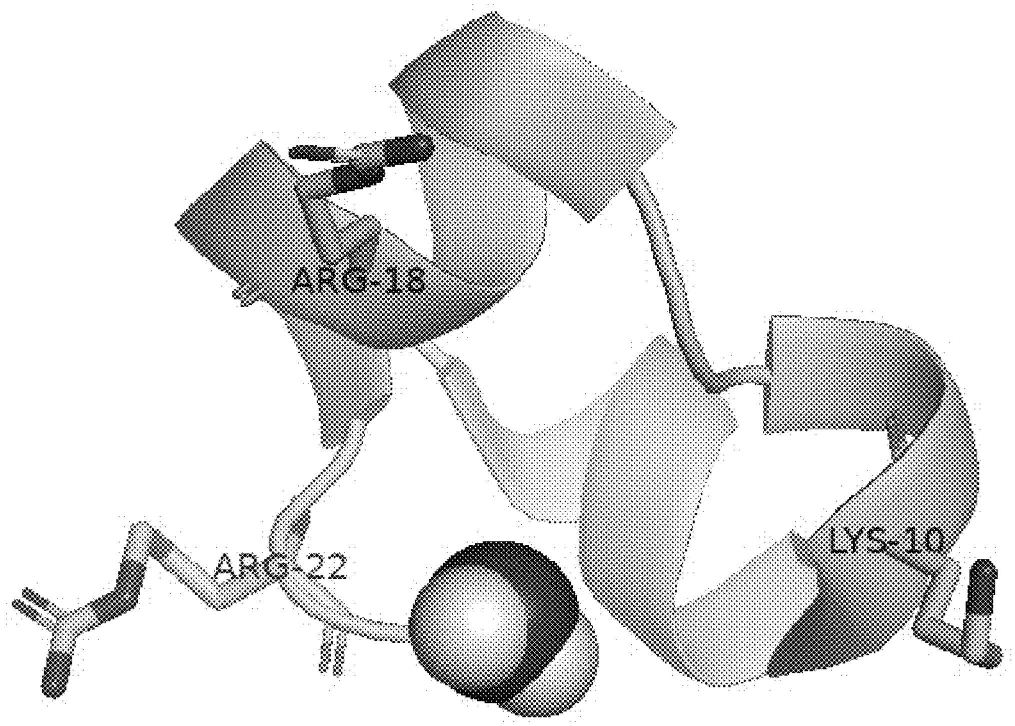
FIG. 1 is a diagram showing a three-dimensional structure of the polypeptide NaV-B.

(6) The result was opened in PyMOL software to obtain images of the three-dimensional structure of the polypeptide NaV-B as shown in FIG. 1, wherein LYS10 represents the lysine residue at the tenth position, ARG18 represents the arginine residue at the eighteenth position, and ARG22 represents the arginine residue at the twenty-second position.

3. Molecular Docking Analysis Between Polypeptide NaV-B and Sodium Channel Protein Nav1.4

Docking analysis was performed by using ZDOCK, a Fast Fourier Transform (FFT)-based, rigid-body protein-protein docking algorithm:

(1) The pdb files of Nav1.4 and the polypeptide NaV-B were prepared.

(2) The files of the receptor and the ligand were opened in the same window in Discovery Studio 4.0.

(3) ZDOCK settings: angular step size=15; ZRank=False; clustering of docking conformations (Top poses=2000; RMSD Cutoff=6.0; Interface Cutoff=9.0; Maximum Number of Clusters=60); parallel computing=True.

(4) ZDOCK was run and a resultant model with the highest score was selected.

(5) The docking model was opened in PyMOL software to analyze the active pocket and docking site.

Figure 2:
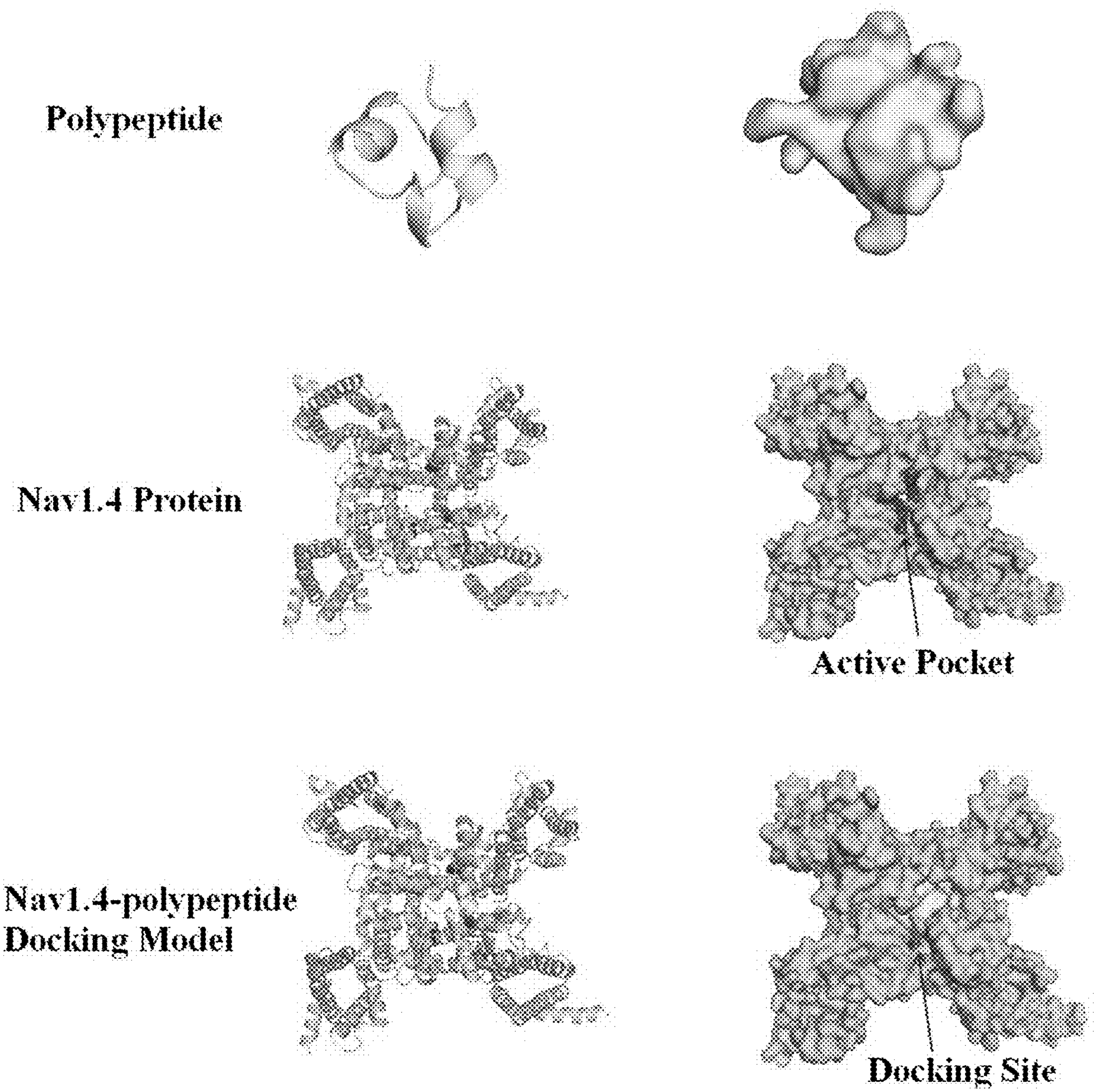
FIG. 2 is a diagram showing the molecular docking between the polypeptide NaV-B and sodium channel protein Nav1.4.

FIG. 2 shows the structures of the polypeptide, Nav1.4 crystal, and docking model of Nav1.4-polypeptide complex, wherein the site indicated by the arrow is the molecular docking site of the active pocket.

Figure 3A:
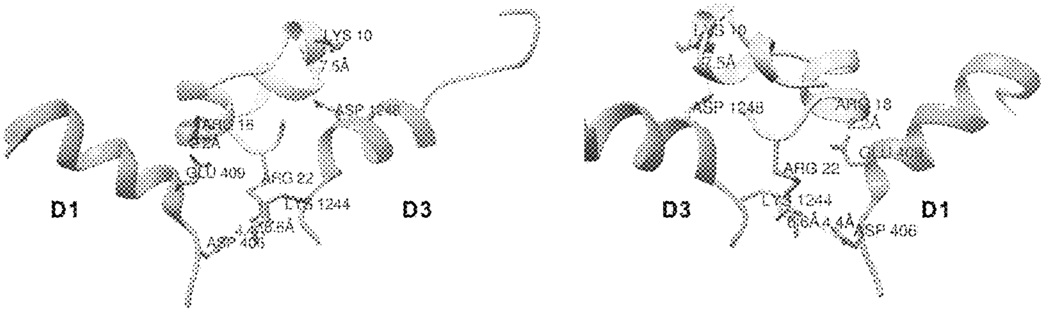
FIG. 3A is a diagram showing docking sites in the complex of NaV-B and Nav1.4 from one perspective.
Figure 3B:
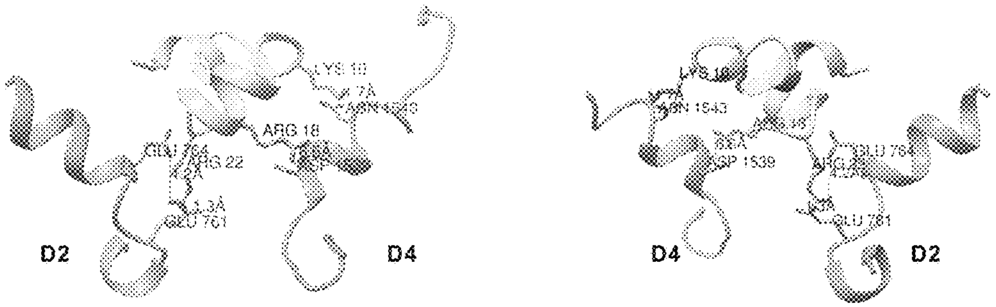
FIG. 3B is a diagram showing docking sites in the complex of NaV-B and Nav1.4 from another perspective.

FIGS. 3A-B shows the docking site in the complex of polypeptide NaV-B and protein Nav1.4, wherein the three-letter abbreviations represent the amino acid residues, and the numbers indicate the positions of corresponding amino acid residues: LYS (lysine), ARG (arginine), ASP (aspartic acid), and ASN (asparagine). The docking pattern in the Nav1.4-NaV-B complex is shown from two perspectives, wherein D1 represents domain 1 of Nav1.4, D2 represents domain 2 of Nav1.4, D3 represents domain 3 of Nav1.4, and D4 represents domain 4 of Nav1.4.

4. Dynamic Simulation Analysis of Nav1.4-NaV-B Complex

Dynamic simulation of Nav1.4 crystal and Nav1.4-NaV-B complex was performed using NAMD and VMD:

(1) We opened the Tk Console in the VMD menu, ran "cd" command to visit the designation folder, ran "mol new filename.pdb" command, and created a psf file using Automatic PSF Builder by calling a top_all27_prot_lipid_na.inp script, loading script information to form a chain and thereby the psf file was created.

(2) A filename.pdb file and a filename.psf file were created, renamed as original.pdb and original.psf We then used "Add Solvation Box" to solvate the protein (boundary=1.5).

(3) We ran minimization.namd to perform energy minimization, wherein the boundary data was obtained by using findbox.tcl, and a par_a1136_lipid_prot carb.prm script was also provided. Energy minimization was realized by running command "namd2+p4 minimize.namd>dummy.out".

(4) A nvt.namd script was provided. Dynamic simulation was performed on the file after energy minimization by running command "namd2+p8 nvt.namd>dummy.out".

(5) The output results were analyzed to give information such as heating results and dynamic potential energy during the dynamic simulation. We then plotted the RSMD by using RMSDplot, and results were as shown in FIG. 4 and FIG. 5.

Figure 4:
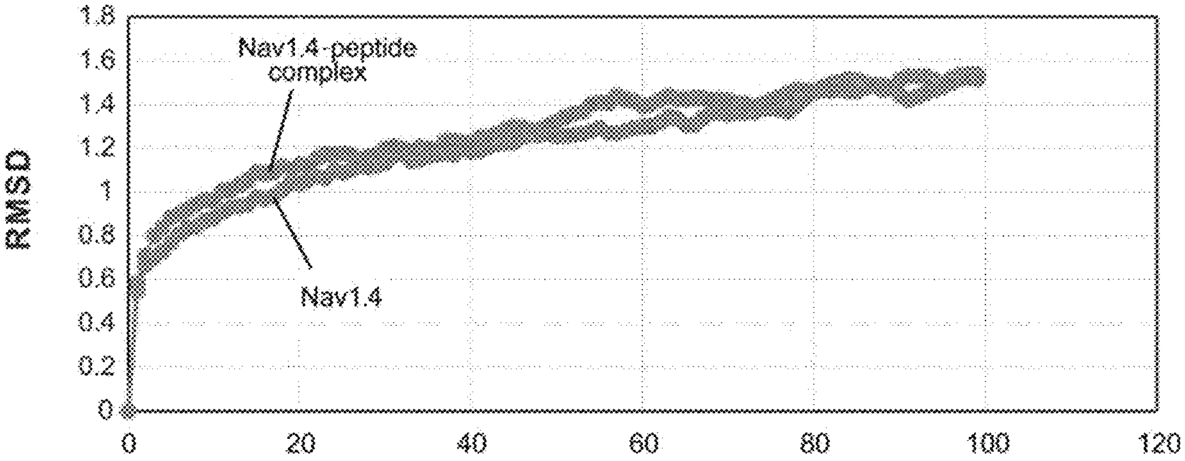
FIG. 4 is a diagram showing the changes in average RMSD of the whole protein by dynamic simulation.

In FIG. 4, the two curves respectively indicate the changes in RMSD of Nav1.4 crystal and Nav1.4-NaV-B complex, which demonstrate the activity of protein backbone during the dynamic simulation.

Figure 5:
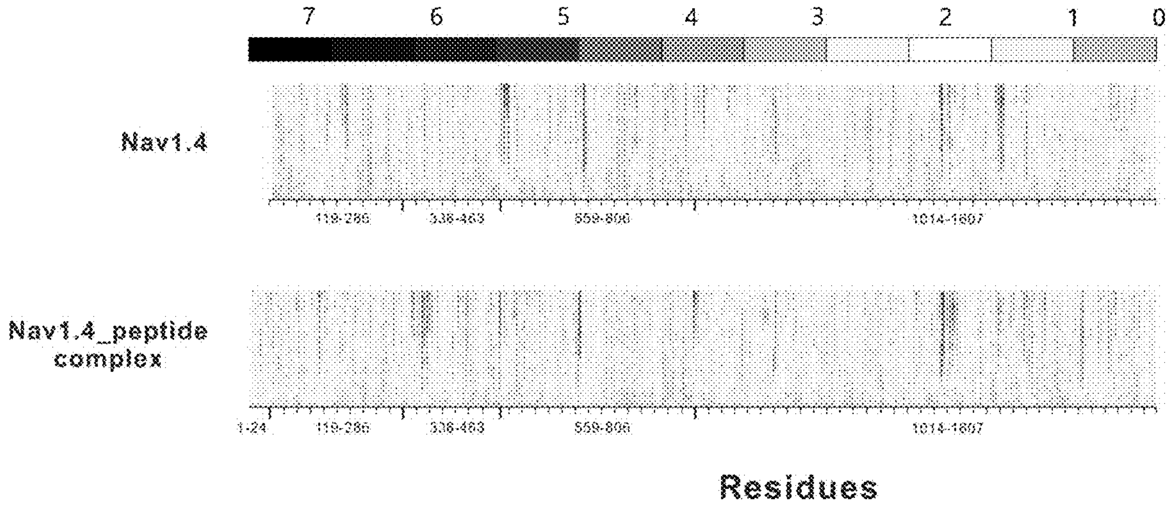
FIG. 5 is a diagram showing the changes in RMSD of each amino acid residue by dynamic simulation.

In FIG. 5, the upper section shows the RMSD of each amino acid residue in Nav1.4 crystal and the lower section shows the RMSD of each amino acid residue in Nav1.4-NaV-B complex. The abscissas refer to the positions of the amino acid residues, and the RMSD values were indicated by the color as shown on the scale.

5. Synthesis of Polypeptide NaV-B (1) The polypeptide can be synthesized by conventional Fmoc solid-phase peptide synthesis. In this embodiment, the polypeptide was synthesized in a synthesizer by Fmoc solid-phase peptide synthesis, accompany with HATU as coupling reagent. 0.2 mmol Wang resin was added to the reaction column. Generally, 3 eq. amino acid was applied for continuous coupling reaction.

(2) Formation of the disulfide bond between Cys-4 and Cys-23

(2a) Deprotection of Cys (Mmt): In a glass reactor equipped with a glass frit, the peptide resin was treated with 2% trifluoroacetic acid (TFA) and dichloromethane (DCM) containing 5% TIS for 10 minutes, and mixed with nitrogen. After filtration, the peptide resin was washed with DCM. The steps of deprotection and washing were repeated for seven times. Finally, the peptide resin was washed with DCM and dimethylformamide (DMF).

(2b) Oxidation of disulfide bond: In a glass reactor equipped with a glass frit, DMF solution with 2 eq. N-chlorosuccinimide (NCS) was applied to treat the free mercaptan peptide resin for 30 minutes, and mixed with nitrogen. After filtration, the peptide resin was washed with DCM. The steps of deprotection and washing were repeated for seven times. Finally, the peptide resin was washed with DCM and DMF.

(3) Formation of the disulfide bond between Cys-3 and Cys-17

(3a) Deprotection of Cys (Acm): In a glass reactor equipped with a glass frit, the peptide resin collected from Step (2) was treated with frozen 95% (95% TFA+2% TIS+1% EDT+2% $H_2O$) for 120 minutes. After filtration, the filtrate was precipitated with cold diethyl ether, and centrifuged at 4000 rpm, followed by freeze-dry to obtain a white solid powder.

(3b) Oxidation of disulfide bond: Peptide was dissolved in water to a final concentration of 1 mg/mL. The peptide suspension was adjusted to pH 8.0 with ammonium bicarbonate, and the mixture was stirred for 12 hours at room temperature. Then, the resulting solution was concentrated and freeze-dried to give a solid powder.

(4) Formation of the disulfide bond between Cys-12 and Cys-24

The solid powder in obtained from Step (3) was dissolved in a 10% acetic acid aqueous solution to a concentration of 5 mg/ml, followed by the addition of 10 eq. iodine. The reaction was monitored by HPLC and MS. After the reaction was complete, vitamin C was added until the mixture became a clear solution, which was then subjected to HPLC and freeze-drying to give the final product.

6. Whole-Cell Patch-Clamp Electrophysiology

Gene encoding human Nav1.4 was inserted into the pcDNA3.1 plasmid between EcoRI and XhoII, so that it can express human Nav1.4 protein. The plasmid was then transfected into HEK293 cells by Lipo 2000. 48 hours after the transfection, G418 was added for selection of stable cell lines, and thereby stable HEK293 cells having G418 resistance. HEK293 cell lines stably expressing human Nav1.4 were verified by Western blot, RT-PCR, and immunofluorescence. The HEK293 cell lines stably expressing human Nav1.4 were subjected to whole-cell patch-clamp electrophysiology using a QPatch-16 system to record the change in membrane potential. Signals were acquired at 25 kHz, and filtered at 8 kHz using Bessel filter. Data will not be considered when the series resistance was greater than 10 MΩ. The HEK293 cells were incubated in a M5650 medium containing 10% fetal bovine serum, 2 mM glutamine, and penicillin. When the cells grew to a concentration of 80%, they were digested with trypsin, resuspended in extracellular buffer and let stand still for 30 minutes. The polypeptide NaV-B was dissolved in intracellular buffer (0.1% fetal bovine serum) to give solutions of different concentrations, and then the NaV-B solutions of different concentrations were each added to the HEK293 cells-containing extracellular buffer and incubated for 5 minutes. The data were collected at room temperature (22° C.). After whole-cell seal formation, the cell was depolarized every 20 seconds from −90 mV to +0 mV under voltage-clamp, where the experiment was conducted at 22-23° C. Currents were measured at a holding potential of −90 mV for a pulse duration of 50 ms, wherein data was correct every 20 seconds. The polypeptide was dissolved in the intracellular buffer, a maximum current where NaV-B was not added was taken as control ($I_0$), and a randomly designed polypeptide (Pep-C) was taken as negative control. The titers of NaV-B and Pep-C were determined through 3-5 rounds of separate experiments. The electrophysiological data was analyzed using PatchMaster v2.20, and the IC50 value was calculated by plotting the current change (I/I0) against concentrations.

Extracellular buffer: 140 mM NaCl, 4 mM KCl, 1 mM $MgCl_2$, 2 mM $CaCl_2$, 5 mM D-glucose, 10 mM HEPES, pH 7.4 (NaOH). Intracellular buffer: 50 mM CsCl, 10 mM NaCl, 60 mM CsF, 2 mM $MgCl_2$, 20 mM EGTA, 10 mM HEPES, pH 7.2 (CsOH).

Figure 6:
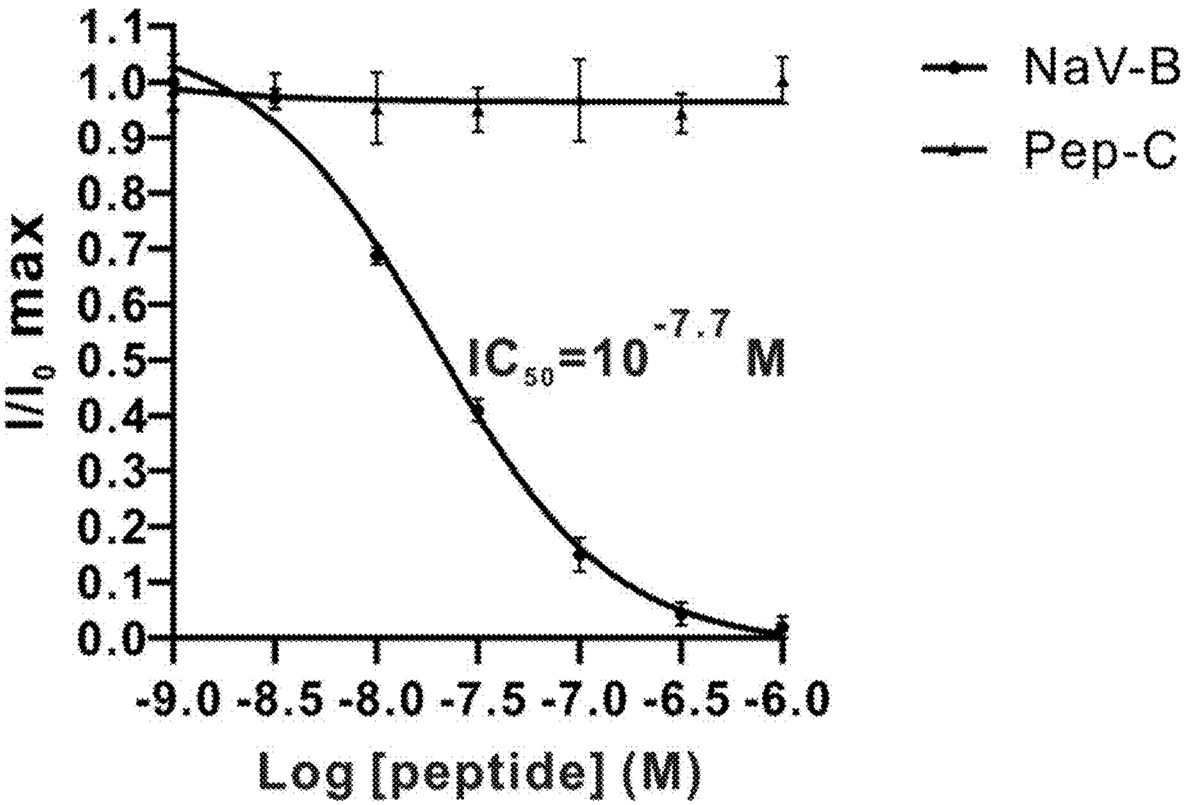
FIG. 6 is a response curve showing the effect of NaV-B on membrane potential, evaluating by whole-cell patch-clamp electrophysiology for 3 to 5 replications. The IC50 value was calculated from a plot of current change (I/I0) against the polypeptide concentration.

Results were as shown in FIG. 6, which illustrated that the polypeptide NaV-B can effectively inhibit the potential change caused by sodium channel protein Nav1.4, with a 50% inhibitory concentration (IC50) of $10^{-7.7}$ M.

7. Use of NaV-B in Reducing Wrinkles

The capacity of NaV-B in reducing skin wrinkles was evaluated by clinical trials, wherein a total of 30 female volunteers ranging from 35 to 55 years old were participating in the trials. In the trials, 0.1 g of lotion was evenly applied to the corners of the volunteers' eyes. The wrinkle volume of each volunteer was measured with a wrinkle analyzer PRIMOS CR at various moments: before application, 15 minutes after application, 1 hour after application, 2 hours after application, and 4 hours after application.

The lotion was prepared by adding NaV-B, glycerin, 1,3-butanediol, sodium hyaluronate, and methylparaben into deionized water according to the following proportions, and stirring until all the ingredients were dissolved.

| Ingredient | Treatment | Control |
|---|---|---|
| NaV-B | 0.0003 wt % | — |
| Glycerin | 5.0000 wt % | 5.0000 wt % |
| 1,3-butanediol | 5.0000 wt % | 5.0000 wt % |
| Sodium hyaluronate | 0.0500 wt % | 0.0500 wt % |
| Methylparaben | 0.1500 wt % | 0.1500 wt % |
| Water | Up to 100 wt % | Up to 100 wt % |

Figure 7:
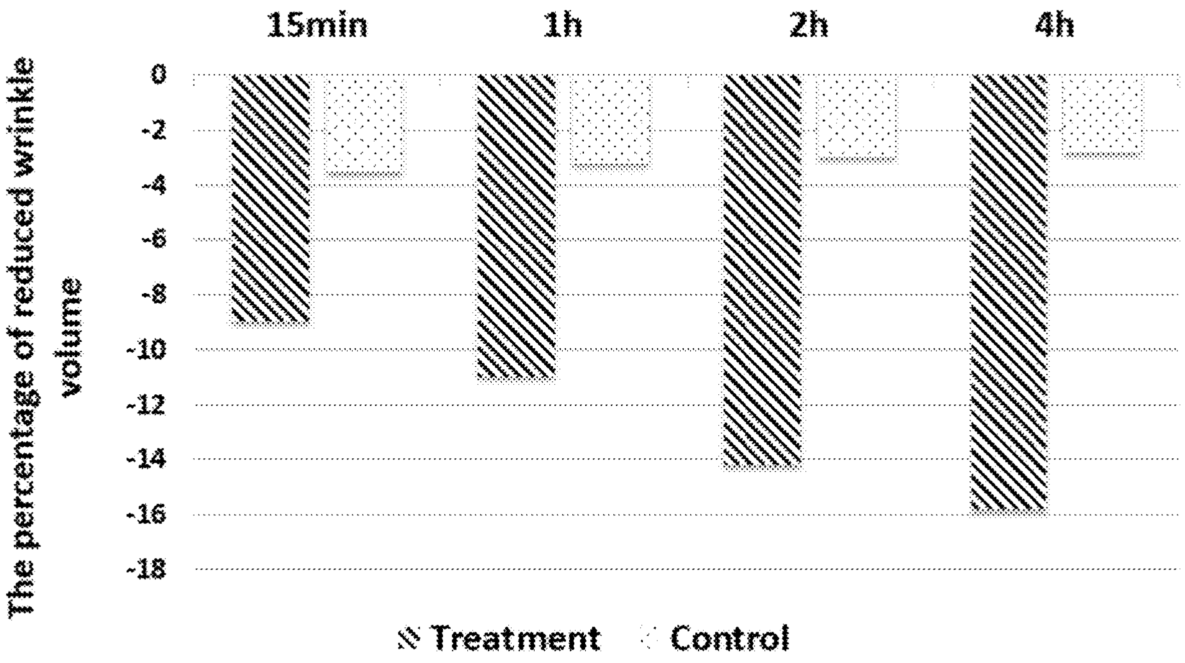
FIG. 7 is a diagram showing the percentage of reduced wrinkle.

Results: The reduced wrinkle volumes of each volunteer were obtained by subtracting the volume measured before application from the volumes measured 15 minutes after application, 1 hour after application, 2 hours after application, and 4 hours after application. The percentages of reduced wrinkle volume of each volunteer were obtained through dividing the reduced wrinkle volumes by the volume measured before application. The average values calculated from all the volunteers were as shown in FIG. 7. The treatment group exhibited a reduction of more than 9% 15 minutes after application, and a reduction of more than 15% 4 hours after application. The control group without the polypeptide NaV-B exhibited significantly lower reduction as compared with the treatment group.

It should be noted that the above embodiments are only used to illustrate the technical solutions of the present invention, but not to limit the scope of the present invention. Although the present invention has been described in detail with reference to the preferred embodiments, those of ordinary skill in the art should understand that the technical solutions of the present invention can be modified or equivalently replaced without departing from the essence and scope of the technical solutions of the present invention.

What is claimed is:

1. A polypeptide having an amino acid sequence of SEQ ID NO:1, wherein the polypeptide comprises a first disulfide bond between Cys-3 and Cys-17, a second disulfide bond between Cys-4 and Cys-23, and a third disulfide bond between Cys-12 and Cys-24.

2. A composition for treating facial or body wrinkles caused by muscle tension, comprising an effective amount of the polypeptide of claim 1 as an active ingredient and a pharmaceutically acceptable carrier.

3. The composition of claim 2, wherein the wherein the pharmaceutically acceptable carrier comprises a component selected from the group consisting of glycerin, 1,3-butanediol, sodium hyaluronate, methyl paraben, water, and combinations thereof.

4. A method for treating facial or body wrinkles caused by muscle tension, comprising administering to a subject in need thereof an effective amount of the polypeptide of claim 1, or administering to the subject a composition comprising the polypeptide as an active ingredient.

5. The method of claim 4, wherein wherein administering comprises topically applying the polypeptide to the subjects skin.

* * * * *